United States Patent [19]
Jenkins

[11] Patent Number: 4,964,309
[45] Date of Patent: Oct. 23, 1990

[54] PORTAL VAPOR DETECTION SYSTEM

[75] Inventor: Anthony Jenkins, North Reading, Mass.

[73] Assignees: Ion Track Instruments, Burlington, Mass.; Ion Track Instruments, Burlington, Mass.

[21] Appl. No.: 311,467

[22] Filed: Feb. 16, 1989

[51] Int. Cl.⁵ .......................................... G01N 31/00
[52] U.S. Cl. ..................................... 73/864.81; 73/23; 73/23.2; 340/632
[58] Field of Search .......... 73/864.33, 864.34, 864.81, 73/864.83, 23; 340/632, 634

[56] References Cited

U.S. PATENT DOCUMENTS

| | | | |
|---|---|---|---|
| 3,883,739 | 5/1975 | Jenkins | 250/304 |
| 3,942,357 | 3/1976 | Jenkins | 73/23 |
| 3,997,297 | 12/1976 | Jenkins et al. | 23/232 |
| 4,019,863 | 4/1977 | Jenkins et al. | 23/232 |
| 4,045,997 | 9/1977 | Showalter et al. | 73/23 |
| 4,116,042 | 9/1978 | Jenkins et al. | 73/23 |
| 4,202,200 | 5/1980 | Ellson | 73/23 |
| 4,242,107 | 12/1980 | Jenkins | 55/18 |
| 4,304,752 | 12/1981 | Jenkins et al. | 422/98 |

OTHER PUBLICATIONS

G. E. Spangler et al., Proceedings of the International Symposium of Analysis and Detection of Explosives, FBI Academy, 3-1983.

*Primary Examiner*—Hezron E. Williams
*Attorney, Agent, or Firm*—Hamilton, Brook, Smith & Reynolds; Hamilton, Brook, Smith & Reynolds

[57] ABSTRACT

A portal vapor detection system for sampling air proximal to the bodies of individuals in which air sampling tubes positioned within movable panels convey a gas flow into an analyzing system. Low vapor pressure materials such as plastic explosives or illicit drugs carried by individuals can be detected thereby enabling the prevention of their transport into aircraft or secured areas.

20 Claims, 2 Drawing Sheets

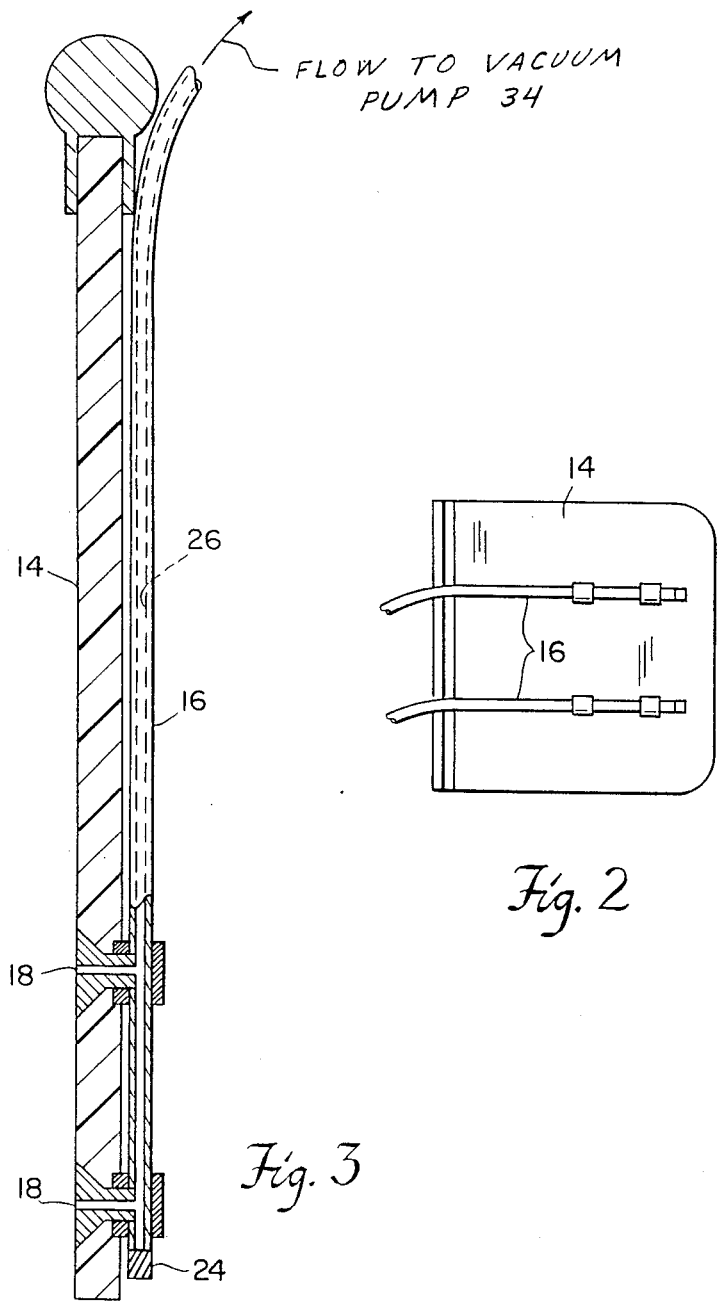

PORTAL VAPOR DETECTION SYSTEM

BACKGROUND OF THE INVENTION

The present invention relates to improvements in vapor sampling techniques for the purpose of detecting contraband and dangerous materials carried by individuals within their clothing. The invention will find particular application in the detection of drugs and explosives carried by persons boarding aircraft or entering secured areas.

Presently, systems exist which detect an illicit substance by detecting the vapors given off by the substance. The detectors may be in the form of a hand-held device or a portal detection system Hand-held detectors can be used to scan people, but this method is slow and not acceptable to the traveling public. Portal detectors, on the other hand, have been designed to rapidly check people for explosives by establishing an air curtain through which the subject is allowed to pass. Any vapor in the clothing is purged out into the air curtain and passes into the detection system. Unfortunately, the available vapor is diluted in the large volume of air passing through the air curtain, and reduces the vapor concentration by as much as 100,000 fold. Reduction of the flow in the air curtain reduces the leeching effect of the flow, increases losses due to natural room air currents and increases the time for the test to an unacceptable level.

The extreme dilution of the vapor renders detection of many materials of interest impossible For example, an explosive such as dynamite may be easily detected because of its high vapor pressure. but many plastic explosives have very low vapor pressure and are not detected in existing air curtain portal systems. Consequently, these devices have not been widely deployed in airports to detect explosives carried on board aircraft even though a serious threat exists.

SUMMARY OF THE INVENTION

The vapor sampling system of the present system samples vapor proximal to the body of a subject to detect the presence of selected materials. The system comprises a number of moveable panels positioned in a doorway through which the subject passes. The moveable panels support a plurality of sampling tubes with intake ports through which vapor samples are drawn. The sampling tubes transport the intake gas flow from the intake ports into a vapor analyzer. The intake ports draw a gas flow from a region proximal to the body of the subject as the panels are displaced by the body of the subject passing through the doorway. The panels are preferably hinged under tension such that they swing along a vertical axis and return to their initial position. The panels are sufficient in size and number to provide the necessary examination of the individuals entire body.

A preferred embodiment utilizes two sets of panels that are placed in the doorway, with each pair of panels being hinged along a vertical axis on opposite sides of the doorframe. Each subject will be encouraged or instructed to push the uppermost panels away from their faces with their hands. The movement of the arms of each subject acts to pump vapors out of the voids in clothing thereby making the vapor available for sampling at the body surface. The body of the subject then displaces the remaining panels in opposite rotational directions as the subject passes through the doorway.

The vapor samples are then drawn from the region proximal to the subject's body through the inlet ports of the sampling tubes of both panels.

The vapor sampling system may include heating means for heating the sampling tubes. The sampling tubes may also be coated on the inside with a material having low absorption properties with regard to the specific gases of interest. The vapor analyzer can be specifically designed or programmed to detect explosives or other illicit materials. By including a signalling means responsive to the vapor analyzer, a signal indicative of the presence of those gases of interest within the vapor analyzer can be generated.

The above, and other features of the invention including various novel details of construction and combination of parts, will now be more particularly described with reference to the accompanying drawings and pointed out in the claims. It will be understood that the particular portal vapor detection system embodying the invention is shown by way of illustration only and not as a limitation of the invention. The principal features of this invention may be employed in various embodiments without departing from the scope of the invention.

BRIEF DESCRIPTION OF THE DRAWINGS

FIG. 2 shows a more detailed rear view of a panel with the sampling tubes extending therefrom.

FIG. 3 is a detailed cross sectional view of the panel, a sampling tube positioned thereon and the ports through which the samples are taken.

DETAILED DESCRIPTION OF THE INVENTION

Figure 1:
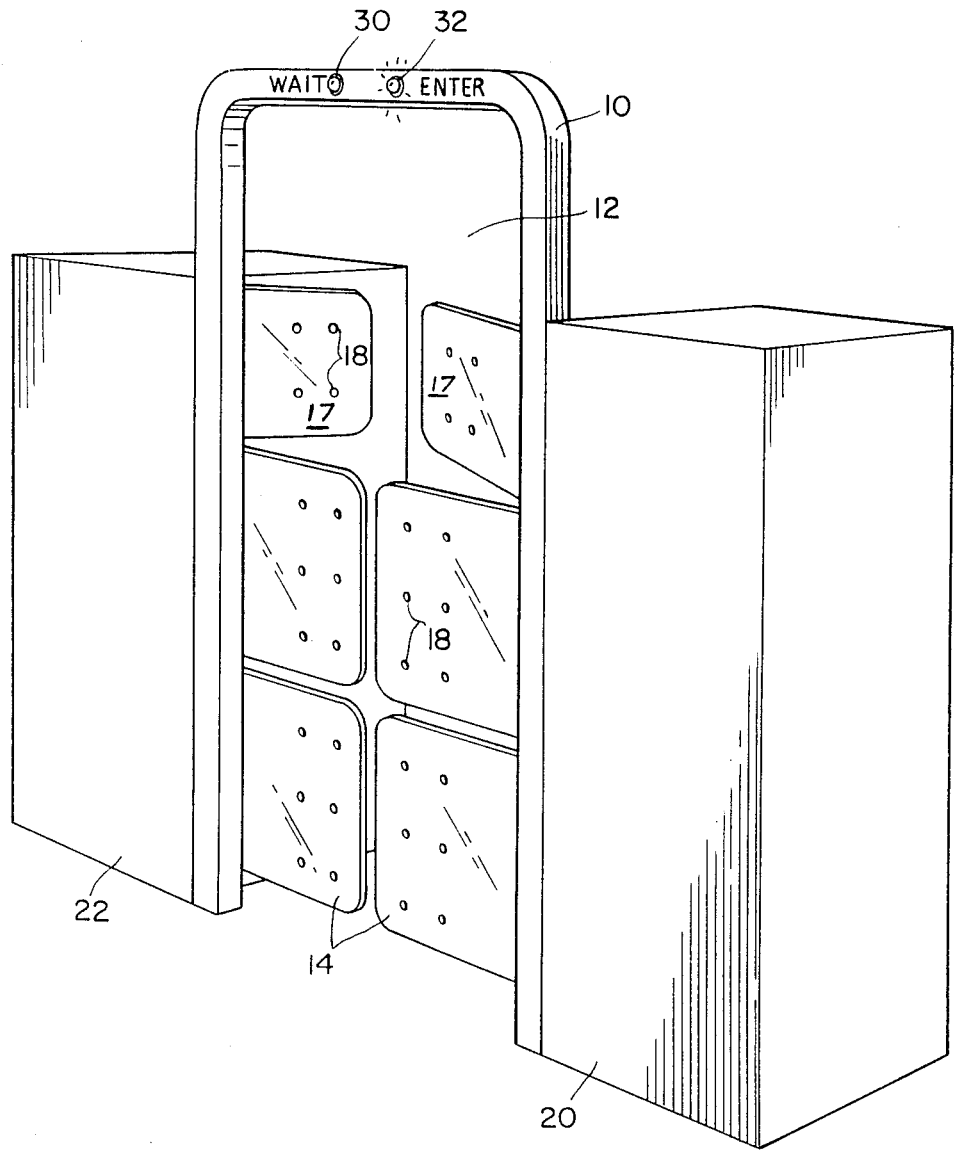
FIG. 1 shows a front perspective view of a preferred embodiment of the vapor sampling system The figure shows the doorway housing the moveable panels each having ports through which vapor samples are drawn.

FIG. 1 shows a vapor sampling system which samples the available vapor from the clothing of a subject without diluting the vapor in a high flow of air. This embodiment enables the detection of a wide range of low volatility substances such as plastic explosives and narcotics, even when those substances are being carried by an individual in a concealed fashion. In particular, plastic explosives made from cyclotrimethyline trinitramine (RDX), and pentaerithritol tetranitrate (PETN) can be detected when carried by individuals in or underneath their clothing.

The front of door frame 10 is shown enclosing doorway 12. Residing in the doorway 12 and attached to doorframe 10 are individually moveable panels 14. each panel having a number of vapor sampling tubes 16 with inlet ports 18 through which an intake gas flow is drawn into the tube. Vapor in the region of the sampling tubes is drawn into the tubes and transported to vapor analyzers 20 and 22. The analyzers detect the presence of any vapors of interest, such as those emanating from explosives or narcotics.

The panels 14 are hinged to the door frame 10 and allowed to swing along a vertical axis in a rotational direction away from the center of the door frame. The doorframe 10 is sized, and the moveable panels 14 are placed such that anyone can pass through the doorway walking upright, and such that the highest moveable panels 17 are level with or above the head of the subject.

In the present embodiment, signal lights 30, 32 at the top of the doorway 12 are provided to alert the subject as to when the doorway should be entered. The signal lights 30, 32 can be controlled manually, by a timer, and can be made responsive to the vapor analyzer. The subject is encouraged to walk through the doorway pushing the upper segments with the hands, so that they move away from the face, and moving the lower panels by pushing through with the body. The action of pushing the upper panels 17 with the hands allows the hands to be rapidly sampled for any vapor by drawing the air from the surface of the hands into the inlet ports 18 of the upper panels 17. The action of lifting the arms disturbs vapor in the clothing, and as the body pushes through the doorway, the panels 14 mechanically disturb the clothing, bringing out vapor that may be contained in the fibers of the clothing and in the voids below the layers of the clothing. The sample tube transports the vapor laden air without further dilution to the vapor analyzer 20, 22.

Substances such as explosives and drugs are capable of emitting characteristic vapors. These vapors are usually termed electron absorbers. An electron capture detector which is sensitive to the presence of electron absorbers can be used in the analyzer 20,22 to detect the presence of the materials of interest. The electron capture detector normally comprises an ionisation chamber containing a source of $\beta$ radiation such as tritium foil or $Ni_{63}$. The detector output is amplified and registered on a meter or other indicating device.

The sampled air is preferably passed through a continuous trapping and desorption process such as that described in U.S. Pat. No 4,242,107 and incorporated herein by reference. This process removes many of the atmospheric components before the vapors are desorbed and passed into the detectors and operates to provide a large concentration gain for the vapors of interest.

The vapor analyzer 20,22 actually employed depends on the type of vapor that is to be detected. Any one of a number of vapor analyzer systems commonly known in the art can be used in conjunction with the present invention. The relatively small volume of gas being sampled and the resulting high sensitivity of the present invention allows different vapor analyzers to function efficiently. Working in conjunction with the vapor analyzer 20,22 is a signalling means output from the vapor analyzer 20,22. A signal, being either audible, visual, or both audible and visual in nature is provided to indicate when the vapors of interest are detected by the vapor analyzer 20, 22. Vapor analyzer 20 and vapor analyzer 22 may work in tandem, or may be designed to detect different vapors if necessary.

FIG. 3 shows in more detail a sampling tube 16 including inlet ports 18 as attached to moveable panels 14. The view is a cross section along a horizontal plane. The left side of the tube 16 faces the front of the vapor sampling system. A vacuum pump can be used to maintain a constant gas flow through each of the intake tubes. Sampling tube 16 is closed at end 24, the side of the panel near the middle of the doorway, and leads past the hinged side of the door to the vapor analyzer. Vapor is drawn in through inlet ports 18 into the tube and is transported into the vapor analyzer through sampling tube 16. In the embodiment of FIG. 3, inlet ports 18 are in front of the sampling system facing the subject entering the doorway.

A preferred embodiment utilizes heating means for heating the sampling tube. The heater is preferably provided by electric wire 26 passing through the length of the sampling tube 16. The sampling tubes, inlet ports and wire coating of this embodiment are made from the material which offers the lowest absorption surface to the vapors of interest. In the case of explosive vapors, a material such as polytetrafluoroethylene (known as TEFLON, a DuPont trade name) would provide a very low absorption surface. By having such a surface, the vapor loss is minimized.

The present invention provides a vapor sampling system with an improved level of sensitivity. Traditionally, detection systems provide responses to a fixed quantity of explosive vapor in proportion to the inverse of the sampling flow rate in which the explosive is entrained. The flows in air curtains previously deployed vary from 30 to 300 liters per second, and the air around the body is sampled in one to ten seconds. The present system employs flow rates in the range from 0.05 to 0.2 liters per second while providing a faster transport time of the vapor to the detector and reducing the time necessary for sampling

I claim:

1. A vapor sampling system for sampling vapor proximal to a body of a subject, the system comprising:
    a vapor analyzer to determine the components of a sample of gas;
    a moveable panel positioned in a doorway. the panel supporting a sampling tube with inlet ports through which vapor samples are drawn, the sampling tube transporting a gas flow from the inlet ports to the vapor analyzer, and the inlet ports drawing the gas flow from a region proximal to the body of the subject as the panel is displaced by the body of the subject passing through the doorway.

2. The vapor sampling system of claim 1 further comprising a vacuum pump to provide the gas flow 3. The vapor sampling system of claim 1 further comprising a plurality of individually moveable panels.

4. The vapor sampling system of claim 3 wherein each panel is hinged such that it swings along a vertical axis.

5. The vapor sampling system of claim 3 wherein each of said plurality of panels are hinged to rotate about one of two parallel vertical axis such that the panels of each axis rotate in opposite directions upon displacement by the subject.

6. The vapor sampling system of claim 1 further comprising heating means for heating the sampling tubes.

7. The vapor sampling system of claim 1 wherein the inner surfaces of the sampling tubes and inlet ports are made from a material having low absorption properties for specific gases 8. The vapor sampling system of claim 1 further comprising signalling means, the signal being generated when the concentration level of a selected vapor is detected by the vapor analyzer 9. A vapor sampling system for sampling the vapor proximal to the body of a subject, the system comprising:
    a tube having an inlet port through which an intake gas flow is drawn, the tube being rotatably mounted within a portal through which the subject passes thereby causing rotation of the tube relative to the portal with the tube being shaped to allow a side of the tube with the inlet port to contact the subject, drawing the intake gas flow from a region proximal to the body of the subject into the tube;

a vapor analyzer with detection means for detecting a vapor;

a suction means for drawing the intake gas flow into the vapor analyzer through the sampling tube; and signalling means for providing a detection signal responsive to the vapor analyzer for indicating the presence of said vapor in the vapor analyzer.

10. The vapor sampling system of claim 9 further comprising heating means for heating the sampling tube.

11. The vapor sampling system of claim 9 wherein the inner surfaces of the sampling tubes and inlet ports are made from a material having low absorption properties for specific gases.

12. The vapor sampling system of claim 9 wherein the vapor analyzer is comprised of a detector to detect explosive materials.

13. A method for sampling the vapor proximal to the body of a subject, the method comprising:

drawing an intake gas flow through the inlet ports of a plurality of sampling tubes, the tubes being attached to a moveable panel residing in a doorway and leading to a vapor analyzer, a sample of vapor being collected from the proximal region of the body of the subject as the moveable panel is displaced by the body of the subject passing through the doorway;

analyzing the vapor with the vapor analyzer to detect a quantity of a vapor of interest as the gas flow is drawn into the vapor analyzer; and providing a signal responsive to the vapor analyzer, the signal issued when the predetermined quantity of the vapor of interest is detected by the vapor analyzer.

14. The method of claim 13 wherein the moveable panel is hinged such that it swings along a vertical axis.

15. The method of claim 13 further comprising a plurality of individually moveable panels each having ports for drawing a gas flow.

16. The method of claim 15 wherein the panels reside in the doorway, each panel having sampling tubes leading to a vapor analyzer such that each moveable panel is hinged along a vertical axis at one side of the doorway where a subject passing through the doorway rotates each panel along its respective vertical hinge axis, allowing vapor samples to be drawn from a region proximal to the subject into the inlet ports of the sampling tubes of each panel.

17. The method of claim 16 wherein the sampling tubes of each panel lead to the same vapor analyzer 18. The method of claim 13 further comprising the step of heating the sampling tubes to heat the gas flow.

19. The method of claim 13 wherein the inner surfaces of the sampling tubes and inlet ports are comprised of a material having low absorption properties with regard to specific gases 20. The method of claim 13 wherein the vapor analyzer detects vapors from explosive materials

* * * * *